United States Patent
Jalali et al.

(10) Patent No.: US 9,903,804 B2
(45) Date of Patent: Feb. 27, 2018

(54) REAL-TIME LABEL-FREE HIGH-THROUGHPUT CELL SCREENING IN FLOW

(71) Applicant: THE REGENTS OF THE UNIVERSITY OF CALIFORNIA, Oakland, CA (US)

(72) Inventors: Bahram Jalali, Los Angeles, CA (US); Ata Mahjoubfar, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 162 days.

(21) Appl. No.: 15/016,217

(22) Filed: Feb. 4, 2016

(65) Prior Publication Data
US 2016/0223453 A1 Aug. 4, 2016

Related U.S. Application Data

(63) Continuation of application No. PCT/US2014/050236, filed on Aug. 7, 2014.
(Continued)

(51) Int. Cl.
*G01N 21/00* (2006.01)
*G01N 15/14* (2006.01)
(Continued)

(52) U.S. Cl.
CPC ..... *G01N 15/1434* (2013.01); *G01B 9/02043* (2013.01); *G01N 15/1429* (2013.01); *G01N 15/1459* (2013.01); *G06K 9/00147* (2013.01); *G06K 9/46* (2013.01); *G06T 7/0012* (2013.01); *G06T 11/60* (2013.01);
(Continued)

(58) Field of Classification Search
CPC ........ G01N 15/14; G01N 21/64; G01N 21/68; G06T 7/00; G06T 11/60; G06K 9/46; G06K 9/36; G06K 9/00; H04N 5/225; G01J 3/44; G01J 3/02; H01J 37/32935; G01B 9/02
See application file for complete search history.

(56) References Cited

U.S. PATENT DOCUMENTS 8,446,593 B1  5/2013  Ellerbee
2005/0058352 A1* 3/2005  Deliwala ............. G01J 3/02
                                                382/232

FOREIGN PATENT DOCUMENTS

WO   2012-039802 A2   3/2012

OTHER PUBLICATIONS

Jalali et al., "Breaking speed and sensitivity limits", Optik &Photonik. 2010, vol. 5, No. 2, pp. 32-36.
(Continued)

*Primary Examiner* — Abdullahi Nur
(74) *Attorney, Agent, or Firm* — O'Banion & Ritchey LLP; John P. O'Banion

(57) ABSTRACT

A label-free imaging-based flow cytometer that measures size and cell protein concentration simultaneously is disclosed. Cell protein concentration adds a parameter to cell classification that improves the specificity and sensitivity of flow cytometers without the requirement of cell labeling. The system uses coherent dispersive Fourier transform to perform phase imaging at flow speeds as high as a few meters per second. To retrieve cell information in real-time, an analog signal processing system based on quadrature phase demodulation is described.

29 Claims, 11 Drawing Sheets

Related U.S. Application Data

(60) Provisional application No. 61/863,405, filed on Aug. 7, 2013.

(51) Int. Cl.
    *G01B 9/02*     (2006.01)
    *G06K 9/00*     (2006.01)
    *G06K 9/46*     (2006.01)
    *G06T 7/00*     (2017.01)
    *G06T 11/60*     (2006.01)
    *G01N 15/00*     (2006.01)
    *G01N 15/10*     (2006.01)

(52) U.S. Cl.
    CPC ............ *G01N 2015/0065* (2013.01); *G01N 2015/1006* (2013.01); *G01N 2015/1087* (2013.01); *G01N 2015/144* (2013.01); *G01N 2015/1454* (2013.01); *G06T 2207/10056* (2013.01); *G06T 2207/30024* (2013.01); *G06T 2207/30242* (2013.01)

(56) References Cited

OTHER PUBLICATIONS

Liang et al., "Determining refractive index of single living cell using an integrated microchip", Sensors and Actuators A: Physical, 2007, vol. 133, No. 2, pp. 349-354.

Goda et al., "Real-time opical reflectometry enabled by amplified dispersive Fourier transformation", Applied Physics Letters, 2008, vol. 93, No. 3, pp. 1-3 (No. 031106 in press).

Mahjoubfar et al., "Label-free high-throughput cell screening in flow", Biomedical Optics Express, Sep. 1, 2013, vol. 4, No. 9, pp. 1618-1625 (E-publication: Aug. 12, 2013).

Korean Intellectual Property Office (KIPO), International Search Report and Written Opinion, PCT/2014/050236, dated Nov. 6, 2014, pp. 1-13, with claims searched, pp. 14-18, corresponding to this application.

\* cited by examiner

REAL-TIME LABEL-FREE HIGH-THROUGHPUT CELL SCREENING IN FLOW

CROSS-REFERENCE TO RELATED APPLICATIONS

This application is a 35 U.S.C. § 111(a) continuation of PCT international application number PCT/US2014/050236 filed on Aug. 7, 2014, incorporated herein by reference in its entirety, which claims priority to, and the benefit of, U.S. provisional patent application Ser. No. 61/863,405 filed on Aug. 7, 2013, incorporated herein by reference in its entirety. Priority is claimed to each of the foregoing applications.

The above-referenced PCT international application was published as PCT International Publication No. WO 2015/021332 on Feb. 12, 2015, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This technology pertains generally to imaging, and more particularly to phase contrast imaging for cell screening.

2. Background Discussion

Flow cytometry is a powerful tool for cell counting and biomarker detection in biotechnology and medicine, especially with regards to blood analysis. Standard flow cytometers perform cell type classification both by estimating size and granularity of cells using forward- and side-scattered light signals and through the collection of emission spectra of fluorescently-labeled cells. However, cell surface labeling as a means of marking cells is often undesirable, as many reagents negatively impact cellular viability or provide activating/inhibitory signals, which can alter the behavior of the desired cellular subtypes for downstream applications or analysis.

Cell protein content measurement can be used in many biomedical applications such as blood doping detection, infection monitoring, drug development and screening, studies of necrosis and apoptosis, cell cycle progression and differentiation, and in cancer diagnostics. Current methods for cell protein concentration measurement include electrical methods based on dielectrophoresis, mechanical methods based on microchannel cantilevers, and optical methods based on scattering patterns, emission spectra of external cavity lasers, and holographic and phase microscopy. These methods are either inherently too slow for high-speed flow cytometry applications, or require feedback mechanisms to provide necessary precision.

Furthermore, size-based classification can also be used for label-free identification of cells of interest in a suspension stream. However, due to significant overlap of size ranges between most mammalian cells, size-based technologies require additional layers of parametric gating to be useful as a diagnostic tool.

BRIEF SUMMARY

Since the refractive index of a cell is proportional to its protein content, the simultaneous measurement of refractive index and size of cells may be predicted to provide two independent parameters for cell classification.

The systems and methods of the present disclosure describe a label-free imaging-based flow cytometer that measures cell size and cell protein concentration simultaneously, either as a stand-alone instrument or as an add-on to conventional flow cytometers. Cell protein concentration adds a parameter to cell classification that improves the specificity and sensitivity of flow cytometers without the requirement of cell labeling. This system uses coherent dispersive Fourier transform to perform phase imaging at flow speeds as high as a few meters per second. Finally, to retrieve cell information in real-time, an analog signal processing system based on quadrature phase demodulation is described.

One aspect of the technology of the present disclosure is a fast and high-precision optical cell density and size measurement method based on serial time-encoded amplified microscopy (STEAM), which captures tens of millions of frames-per-second with sub-nanosecond shutter speed. The systems and methods of the present disclosure incorporate a novel configuration of STEAM capable of high-speed phase microscopy and demonstrating label-free single-cell classification and diagnostics. In addition, the systems and methods of the present disclosure minimize loss and chromatic aberration, decrease polarization sensitivity, and result in a smaller footprint. The technology of the present disclosure also employs reflective optics.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Serial time-encoded amplified microscopy (STEAM) primarily involves two steps that are both performed optically. In the first step, the spectrum of a broadband optical pulse is converted by a spatial disperser into a rainbow that illuminates the target. Therefore, the spatial information (image) of the object is encoded into the spectrum of the resultant reflected or transmitted rainbow pulse. A 1D rainbow is used in flow imaging as the flow causes the cell to be scanned in the second dimension. In the second step, the spectrum of the image-encoded pulse is mapped into a serial temporal signal that is stretched in time to slow it down such that it can be digitized in real-time. This optically-amplified time-stretched serial stream is detected by a single-pixel photodetector and the image is reconstructed in the digital domain. Subsequent pulses capture repetitive frames, hence the laser pulse repetition rate corresponds to the frame rate of STEAM, and the shutter speed (exposure time) corresponds to the temporal width of the pulse. STEAM enables high speed real-time imaging and photonic time stretch for digitizing fast images in real-time and the optical image amplification for compensating the low number of photons collected during the ultra-short shutter time.

The systems and methods of the present disclosure employ a novel Coherent-STEAM system to capture phase images of cells/particles in flow. A Michelson interferometer is used to map the phase image of cells into the spectrum of broadband optical pulses. This phase imaging technique exploits the fast shutter speed of STEAM to freeze path length fluctuations of interferometer arms and attains nanometer phase resolution with no need for feedback stabilization of the interferometer. The Coherent-STEAM methods of the present disclosure were used to measure the refractive index of individual cells in an imaging flow cytometer by simultaneous measurement of size and total optical phase-shift induced by the cells. To show efficacy for one exemplary application, the label-free STEAM-based cell classifier of the present description was used to distinguish OT-II T cell hybridoma from SW480 epithelium cancer cells. It was shown that adding protein concentration to size as an additional classification parameter increases accuracy and specificity in flow cytometry.

Figure 1:
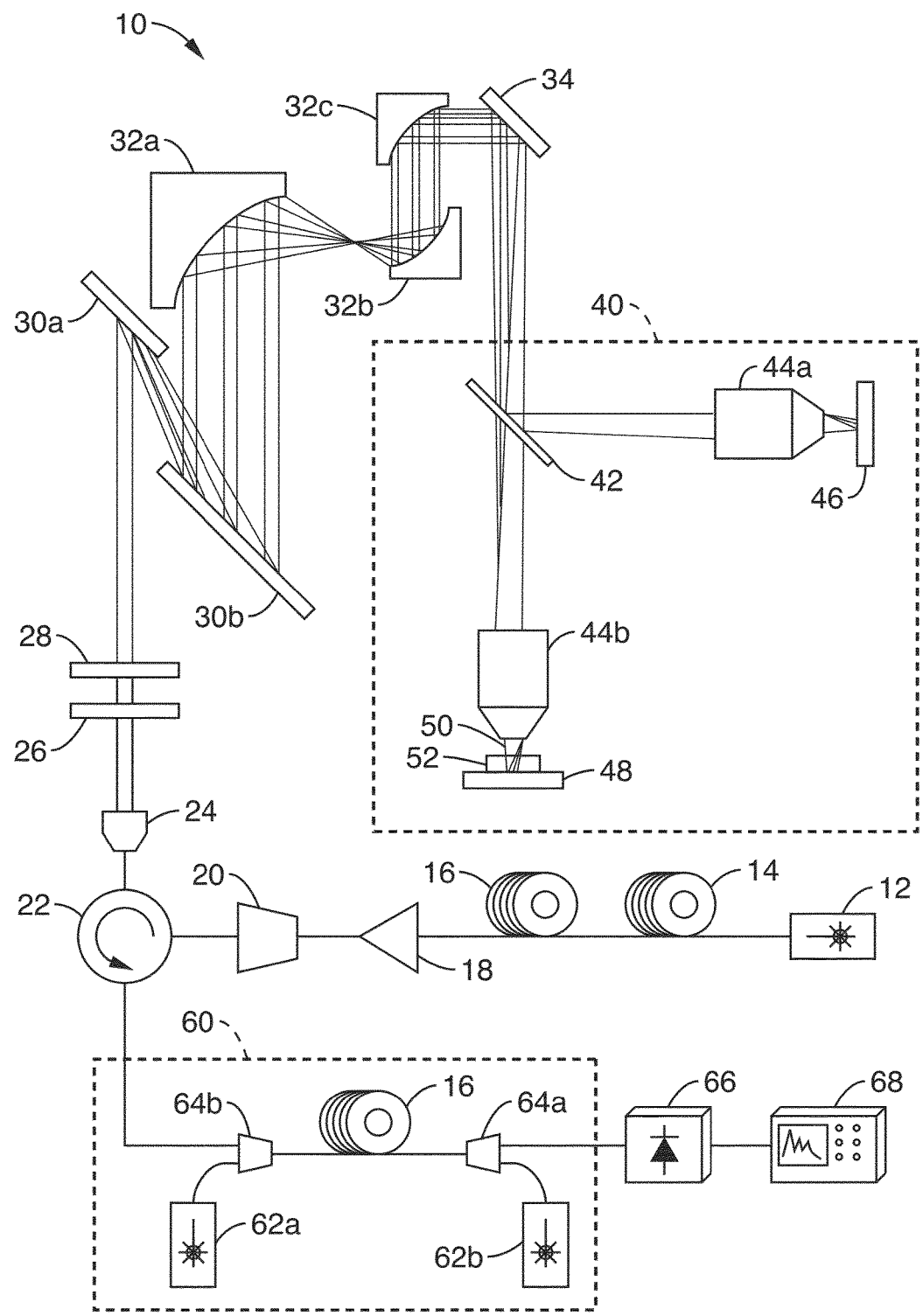
FIG. 1 is a schematic view of a Coherent-STEAM system in accordance with the present description.

FIG. 1 shows a schematic diagram of Coherent-STEAM system 10 in accordance with the present disclosure. System 10 incorporates a combination of a STEAM module 60 and a Michelson interferometer 40 for fast and high-precision optical cell density and size measurement.

A mode-locked fiber laser 12 generates pulses at 1565 nm with a repetition rate of 36.128 MHz and a pulse width slightly less than 100 fs. Pulses are spectrally broadened with a highly nonlinear fiber 14 to approximately 100 nm bandwidth. A short dispersion compensating fiber 16 with an overall dispersion of 60 ps/nm is used to temporally broaden pulses to 1.2 ns, allowing an erbium doped fiber amplifier (EDFA) 18 to amplify the pulses with limited or no distortion. Amplified pulses then enter a coarse wavelength division multiplexing (WDM) filter 20, and the output of the 1591 nm channel is used to shape laser pulses with a considerably flat spectrum over a 1581 nm to 1601 nm bandwidth. These pulses pass through an optical circulator 22 and are coupled to free-space with a fiber collimator 24.

The free-space laser pulses are linearly polarized with a quarter-wave plate 26 and half-wave plate 28, and then they are spatially dispersed with a pair of reflection diffraction gratings 30a and 30b, so that each wavelength component of the collimated beam is positioned at a different lateral point, similar to a rainbow. Thus, a 1D rainbow is generated with different wavelength components imaging different points on the cells flowing in a microfluidic channel.

A set of 90 degree off-axis parabolic mirrors 32a and 32b, with 152.4 mm and 25.4 mm reflected focal lengths are used to form a beam reducer that shrinks the rainbow beam 6 times. Parabolic gold-coated mirrors are ideally used to minimize loss, aberration, and polarization sensitivity. In addition, a 15 degree off-axis parabolic gold-coated mirror 32c with 635 mm reflected focal length and a 0.4 numerical aperture long working-distance objective lens further shrink the rainbow to an about 130 μm field of view. Using reflective optics, the signal-to-noise ratio was improved by about 9 dB.

After reflecting off mirror 34, pellicle beam-splitter 42 and two identical long working-distance objective lenses 44a and 44b are used to form two arms of the interferometer 40 for phase measurement. Back apertures of objective lenses are fully illuminated with each wavelength component of the broadband mode-locked laser pulses to ensure diffraction-limited resolution. Different wavelength components of the rainbow are focused on reference mirror 46 in the reference arm and on the reflective substrate 48 of a microfluidic device 52 in the sample arm. Cells hydrodynamically focused at the center of the channel flow at a velocity of 1.3 m/s. The microfluidic device 52 comprises a shallow channel configured to align cells within the focal depth of the system.

The rainbow pulses 50 pass through the cells and are reflected back by the mirror substrate 48 of the microfluidic device 52. The total bandwidth of the pulses 50 interrogating the cells in the Coherent-STEAM system 10 is less than 20 nm centered at 1590 nm, giving a negligible fractional bandwidth of 1.3%. Therefore, the color-dependency of absorption is very small and can be easily neglected.

The reflected pulses from the microfluidic device 52 and reference mirror 46 interfere at the beam splitter 42 and return to the fiber, where they are directed with the optical circulator 22 and to an amplified time-stretch system 60 that chirps, stretches, and amplifies each pulse, so that different wavelength components reach the photodetector serially.

The amplified time-stretch system/module 60 is a combination of a Raman amplifier (incorporating wavelength division multiplexers 64a and 64b) and a dispersive fiber 16 to perform dispersive Fourier transform. Four Raman pump lasers (only lasers 62a and 62b are shown in FIG. 1) at 1450 nm, 1470 nm, 1490 nm, and 1505 nm are used to amplify the signal for about 15 dB over the whole optical bandwidth uniformly. The dispersive fiber 16 chirps and stretches each pulse in time to about 27 ns. Accordingly, different wavelength components reach the photodetector serially. An analog-to-digital convertor (ADC) 68 with a sampling rate of 50 GSps and 20 GHz bandwidth is used to acquire the output signal of the photodetector 66.

Figure 2:
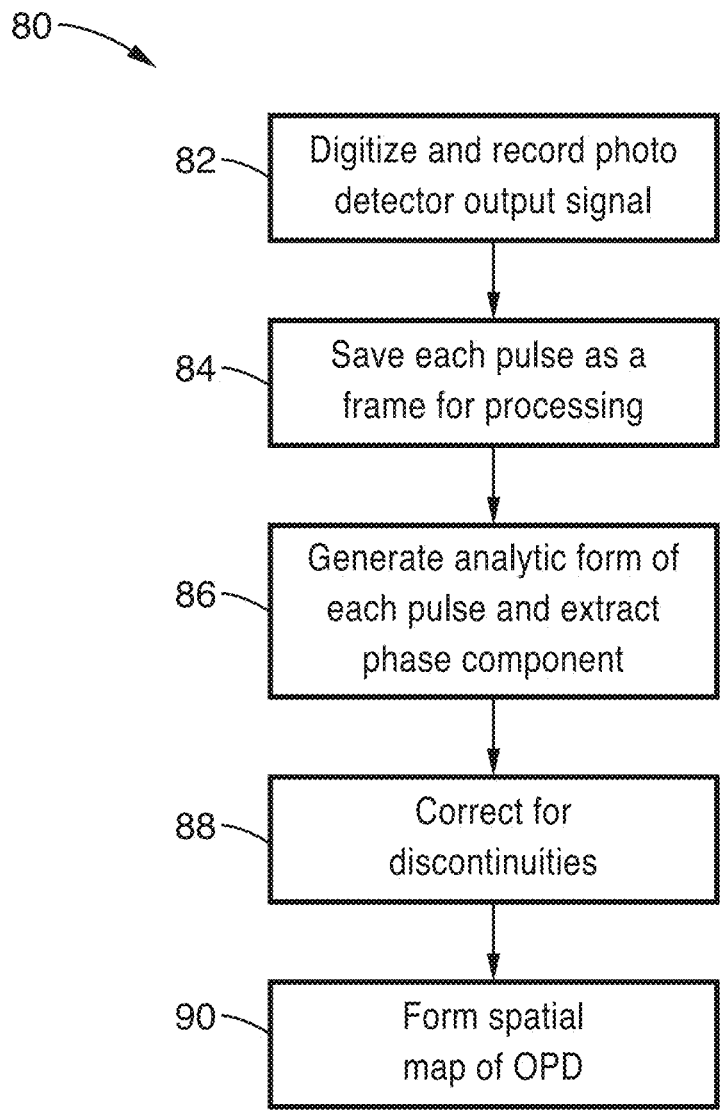
FIG. 2 shows a flow diagram for the Coherent-STEAM digital signal processing method of the present description.

FIG. 2 and FIG. 3A through FIG. 3F show the digital signal processing of Coherent-STEAM data in accordance with the present description. FIG. 2 shows a flow diagram for the Coherent-STEAM digital signal processing method 80, while FIG. 3A through FIG. 3F show the output for the steps in the signal processing method of FIG. 2.

Figure 3A:
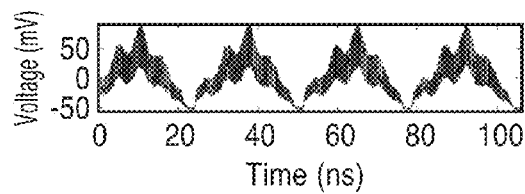
FIG. 3A through FIG. 3F show the output for the steps in the signal processing method of FIG. 2.
Figure 3B:
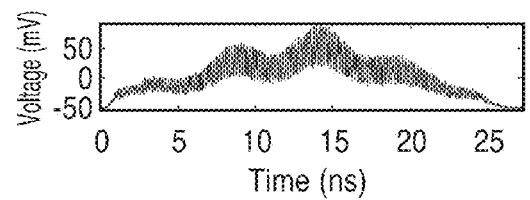

At step 82, the photodetector 66 output signal, I(t), is digitized and recorded by the ADC 68. This signal, illustrated in FIG. 3A, shows sequential laser pulses. Each pulse is used to form one line image. Therefore, the boundaries of pulses are determined precisely, and each pulse (as illustrated in FIG. 3B) is saved separately as a frame for further processing at step 84.

Figure 3C:
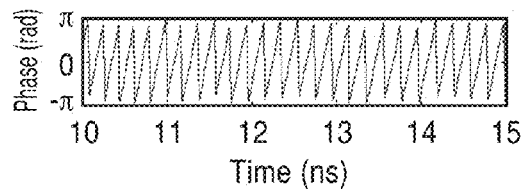

The analytic form of each pulse is generated using Hilbert transformation after the low frequency components corresponding to intensity variations are filtered out. At step 86, the phase component of this analytic form is extracted, while its amplitude component is discarded (FIG. 3C).

Figure 3D:
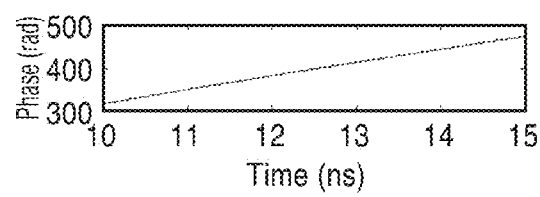

Because the phase varies over a wide range (much larger than $2\pi$ radians), it shows unrealistic discontinuities. An unwrapping algorithm is used to fix these discontinuities at step 88, and the result shows an approximately linear phase increase over the time for each pulse or frame (FIG. 3D). The unwrapping algorithm adds multiples of $\pm 2\pi$ to make the absolute jumps between consecutive samples in a frame smaller than 7 radians when they are greater than $\pi$ radians.

Figure 3E:
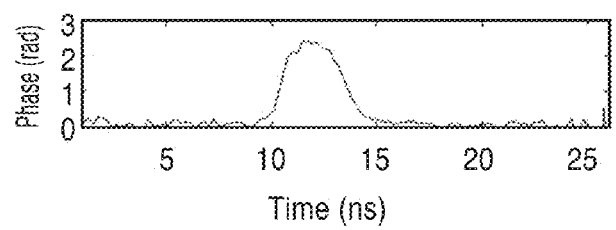
Figure 3F:
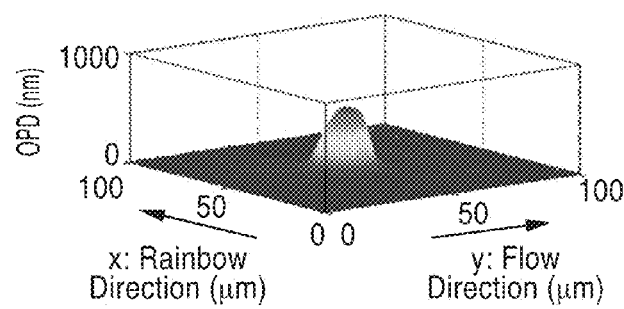

If the linear component of the phase, which corresponds to the fringe (modulation) frequency, $f_m$, due to the interferometer arms' length mismatch, and the background phase level, $\phi_0$, are subtracted, the phase shift induced by the cells in the optical pulse can be observed, as shown in FIG. 3E; i.e.:

$$\Delta\phi(t) = \text{unwrap}(\arg(I_{BP}(t) + j \cdot \hat{I}_{BP}(t))) - 2\pi f_m t - \phi_0 \quad \text{Eq. 1}$$

in which $I_{BP}(t)$ is a band-pass filtered form of I(t) with only spectral features modulated at $f_m$, and $\hat{I}_{BP}(t)$ is the Hilbert transform of $I_{BP}(t)$. Many phase line images generated from subsequent frames are combined at step 90 to form a spatial map of optical path difference (OPD) in two dimensions (shown in FIG. 3F). Since we know the mapping of space to time from the rainbow characteristics and flow speed, OPD at each point is calculated as:

$$OPD(x, y) = \frac{\lambda(x)}{2\pi}\Delta\varphi(x, y) \quad \text{Eq. 2}$$

where x and y are coordinates in the rainbow and flow directions, respectively; $\lambda(x)$ is the wavelength at position x along the rainbow; and $\Delta\phi(x, y)$ is the phase shift induced by the cell at point (x, y).

Spatial mapping of optical path difference can be used to extract the refractive index contrast between the cell and the surrounding liquid. If the thickness of the cell at point (x, y) is t(x, y):

$$OPD(x, y) = 2\Delta n_{cell} \cdot t(x, y) \quad \text{Eq. 3}$$

where $\Delta n_{cell} = n_{cell} - n_{liquid}$ in which $n_{cell}$ and $n_{liquid}$ are the refractive indices of the cell and the surrounding liquid, respectively. The factor 2 is to account for the fact that each wavelength component passes the cell twice in Michelson interferometer. If we integrate Eq. (3) over the area of the cell, we can derive an average refractive index contrast, which corresponds to protein concentration of the cell:

$$\Delta n_{cell} = \frac{\iint_{cell} OPD(x, y)\,dx\,dy}{2V} \quad \text{Eq. 4}$$

where $V = \iint_{cell} t(x, y)\,dx\,dy$ is the volume of the cell. Most of the cells relax to a spherical shape when they are released from substrates and brought into suspension. Therefore, if we know the diameter of the cell, d, we can estimate its volume as $V \cong \pi d^3/6$.

Figure 4:
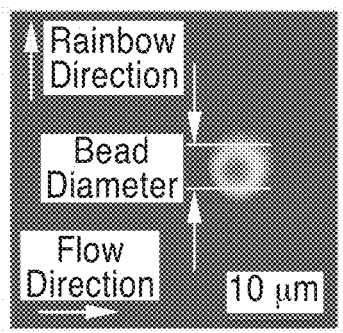
FIG. 4 shows an image demonstrating a method used to find the beads in a spatial map of optical path difference and measure the diameter.
Figure 5A:
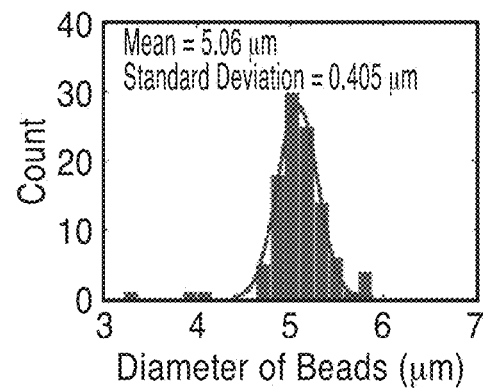
FIG. 5A is a histogram of bead diameters, demonstrating that the measured size distribution has an expected mean of 5 μm and a standard deviation within the range of optical resolution limit.
Figure 5B:
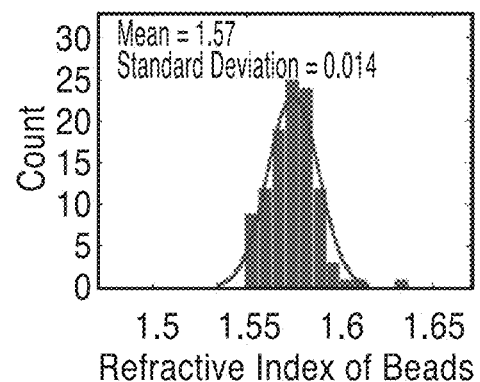
FIG. 5B is a histogram of the refractive index of the beads of FIG. 4.

FIG. 4 through FIG. 5B show a calibration process to calibrate the image processing algorithm/method 80 for size measurements. Spherical polystyrene beads with a NIST traceable diameter of 5 μm were used to calibrate the image processing algorithm for size measurements. A method was developed (using CellProfiler software) to detect the beads or cells in spatial map of optical path difference.

As shown in FIG. 4, bead or cell diameter is measured along the rainbow direction to eliminate size measurement inaccuracies caused by fluctuations of flow speed. Due to limited optical resolution of the setup, the bead or cell edges are blurred, generating a small phase signal outside of the diameter bars. The diameter along the rainbow direction is equal to the diameter along the interrogation optical beam for spherical-shape beads or cells in suspension, including the samples in our experiments.

Histogram analysis of bead diameter distribution for more than one hundred beads with corresponding Gaussian fit to measurements demonstrates that the measured size distribution has a standard deviation of 0.4 μm and an expected mean of 5 μm (as shown in the graph of FIG. 5A). The broadening in the distribution is caused by the limited lateral optical resolution of the Coherent-STEAM setup. This resolution is measured by the knife-edge method and is about 2.5 μm. Therefore, the standard deviation of the bead size distribution is well below the optical resolution.

Referring to FIG. 5B, the refractive index contrast of each bead and the surrounding liquid were measured using Coherent-STEAM. Assuming that the refractive index of water is 1.317 at the 1581 nm to 1601 nm bandwidth, we derived the refractive index of the beads using Eq. (4).

Analysis of the bead refractive indices and corresponding Gaussian fit demonstrates that the beads have a mean refractive index of 1.57 with a standard deviation of 0.014. The coefficient of variation for the bead refractive indices was observed to be 0.89%, which is much smaller than the coefficient of variation for the bead diameters (8.00%). This is expected because all the beads are made out of the same material, while their diameter measurements are effected by dispersity of the size and limited spatial resolution of the setup.

Figure 6A:
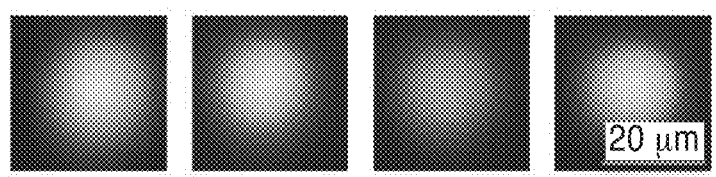
FIG. 6A and FIG. 6B show images of OTII and SW480 cells, respectively, taken by the Coherent-STEAM system of FIG. 1.
Figure 6B:
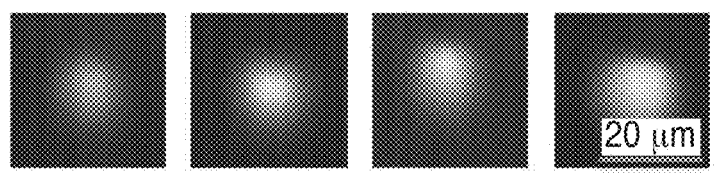
Figure 7:
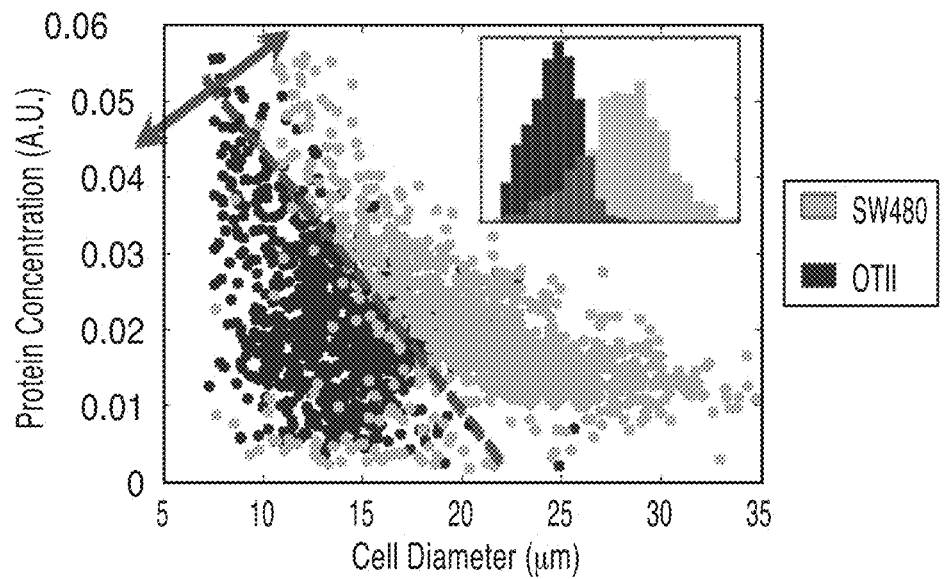
FIG. 7 shows a scattering plot of cell protein concentration (refractive index difference) versus diameter for OTII and SW480 cells.
Figure 8:
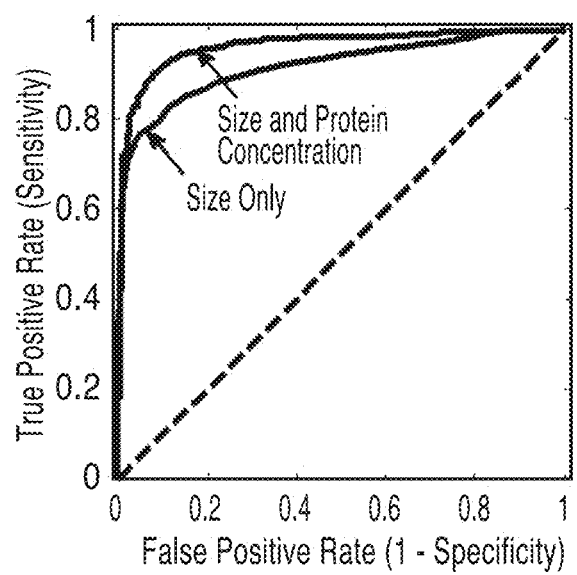
FIG. 8 shows a plot of ROC curves comparing size measurement only to that of simultaneous size and protein concentration measurement.

The calibrated Coherent-STEAM system 10 was then used to measure cell diameter and refractive index contrast (as a measure for protein concentration) simultaneously. Different types of cells have different mean diameters and protein concentrations; however, both of these parameters have a broad range of variations for each cell type. It has been observed that identification of cells is more specific using both of these parameters simultaneously, instead of each individually. Images of OTII (FIG. 6A) and SW480 (FIG. 6B) cells taken by Coherent-STEAM setup demonstrate that the cells are spherical in the microfluidic channel. FIG. 7 shows a scattering plot of cell protein concentration (refractive index difference) versus diameter is shown for OTII and SW480 cells (with total count in upper inset). Using points in a normal range of protein concentration and sliding the detection limit along the depicted direction (perpendicular to the optimum classification line), a receiver operating characteristic (ROC) curve was generated (FIG. 8). Comparing the ROC curve of individual parameters (e.g. size measurement only) to that of simultaneous measurement, the considerably improved detection sensitivity is evident.

In order to process the data for a large number of cells in real-time, the phase recovery from the photodetector output signal is ideally performed almost instantaneously. However, this signal has a high-bandwidth, and a very high-speed analog-to-digital converter (ADC) is generally used to capture it. The high sampling rate of ADC means that the central processing units (CPUs) and field-programmable gate arrays (FPGAs) should process an extremely large number of data points at very high-speeds in real-time, which is impractical. As a solution, the present disclosure incorporates an analog preprocessing of Coherent-STEAM data. The methods of the present disclosure are based on using radio-frequency and microwave telecommunication components to convert output of the Coherent-STEAM system 10 to a set of lower bandwidth signals with slower variations in time, so that the sampling rate of the ADCs required for acquiring them can be much smaller. As a result, the CPUs and FPGAs can handle processing these slower signals and retrieve the phase in real-time.

Figure 9:
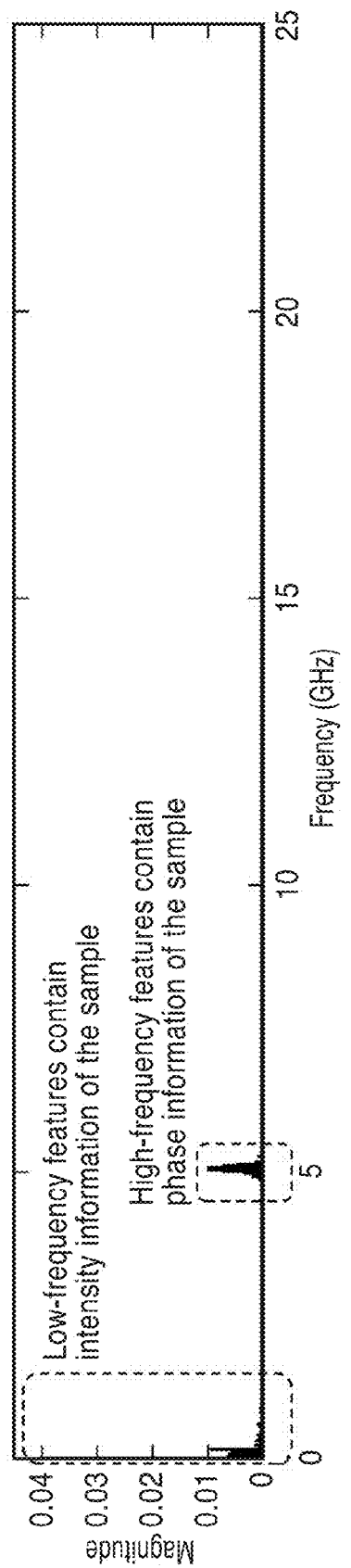
FIG. 9 is a plot of the spectrum of the output signal having two separate spectral bands for the Coherent-STEAM system of FIG. 1.
Figure 10:
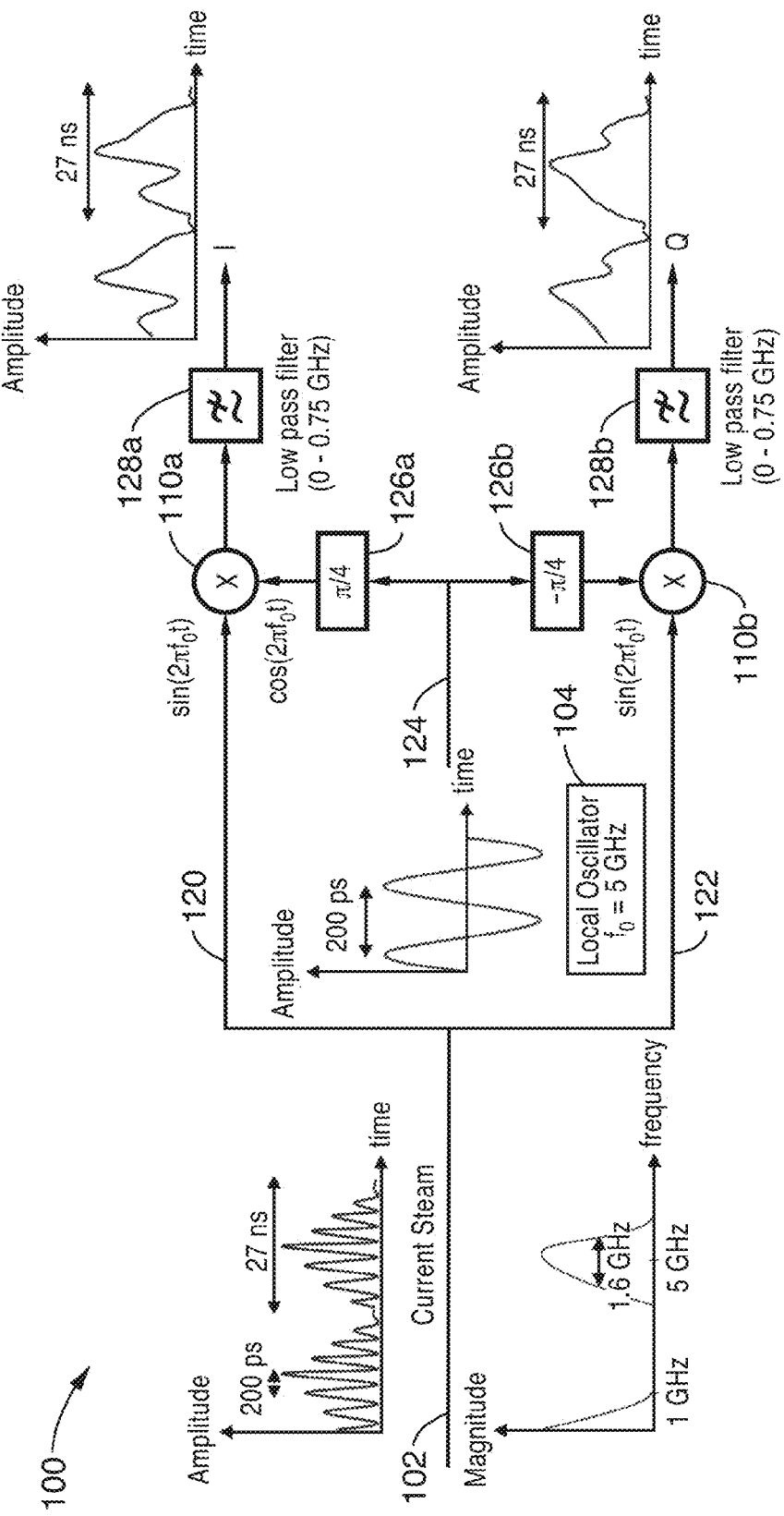
FIG. 10 shows a process flow diagram for an analog signal processing system based on down-conversion of high-frequency spectral components of the Coherent-STEAM output.

FIG. 9 and FIG. 10 detail an analog signal processing technique based on down-conversion of high-frequency spectral components of the Coherent-STEAM output. If the arms' length mismatch in Coherent-STEAM interferometer 40 (see FIG. 1) is chosen to be long enough, two separate features in the spectrum of the system output corresponding to intensity and phase of the sample (as illustrated in FIG. 9). The low frequency components correspond to the intensity of the sample, while the high frequency components contain phase information of the sample. The important assumption here is that the intensity fluctuations along the sample should not be very fast. For example, if the intensity of the cell suddenly drops at a point, there will be a high frequency component in the output (interferogram) because of that drop, and in that case, the phase of the sample will not be a distinguishable high-frequency feature in the spectrum. In the example shown in FIG. 9, the modulation (fringe) frequency of the signal carrying the phase information is approximately 5 GHz.

Figure 11:
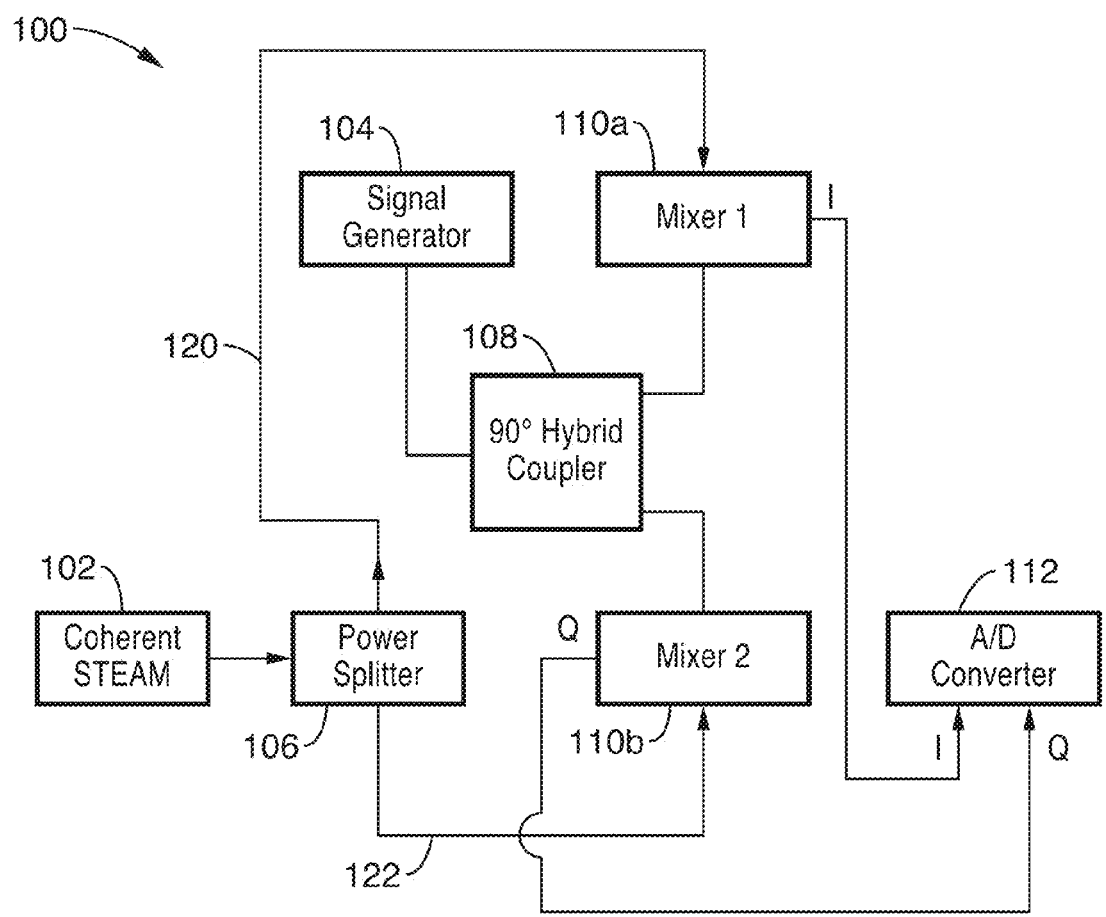
FIG. 11 shows an exemplary component diagram for the system of FIG. 10.

In one preferred embodiment shown in FIG. 10 and FIG. 11, an exemplary analog signal processing system 100 is based on quadrature phase demodulation. First, the Coherent-STEAM signal 102 is split into two paths 120 and 122 via splitter 106. These signals are mixed with two sinusoidal signals 126a and 126b that are 90° phase-shifted with respect to each other. The frequency of the sinusoidal signals is roughly at the modulation frequency of Coherent-STEAM system 10, which is set by arm's length mismatch (in this exemplary setup 5 GHz). Mixers 110a and 110b (FIG. 11) shift the high-frequency components containing the phase information of the Coherent-STEAM output to smaller frequencies close to DC (base band). Finally, the baseband component, which now contains the sample's phase information, can be filtered out with low pass filters 128a and 128b and digitized with an ADC 112 that has a considerably smaller sampling rate than what was required before the down conversion. In addition, because the outputs are mixed with 90° phase-shifted sinusoidal signals 126a and 126b, the phase signal can be derived with a simple calculation as shown in Eq. 5:

$$\phi(t) = \text{unwrap}(\arg(I(t)/Q(t))) \qquad \text{Eq. 5}$$

where I(t) and Q(t) are the outputs of the analog signal processing system as detailed in FIG. 10.

To generate 90° phase-shifted sinusoidal signals, we used a signal generator 104, which is connected to a 90° hybrid coupler 108. The I(t) and Q(t) outputs of the analog signal processing system are captured with a 50 GS/s, 20 GHz bandwidth analog-to-digital converter 112.

Figure 12A:
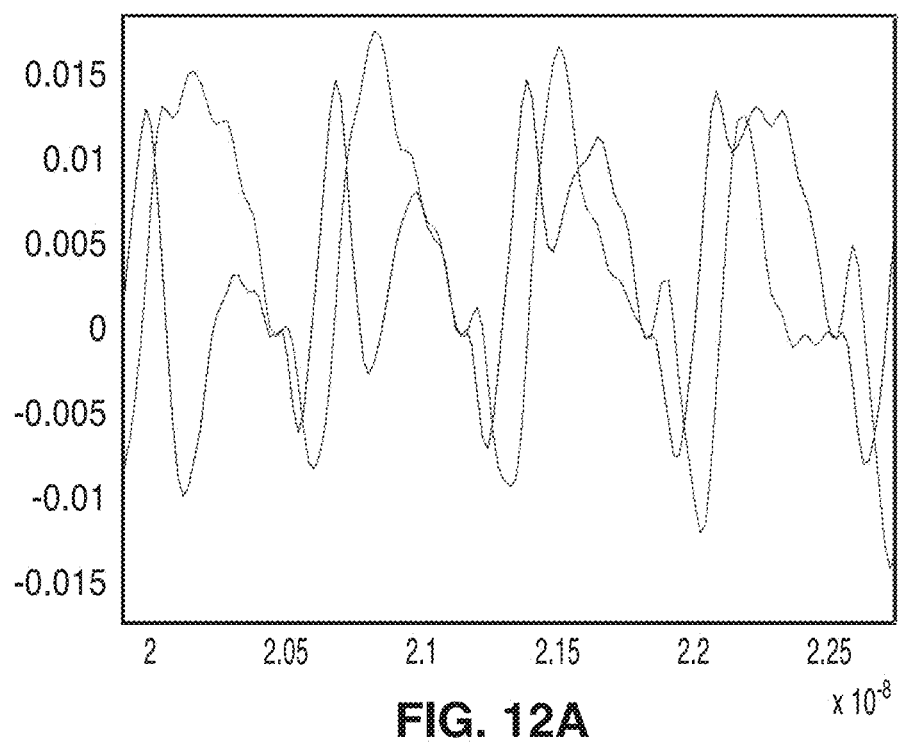
FIG. 12A through FIG. 12D show images illustrating I and Q outputs (FIG. 12A) for the system of FIG. 10 and FIG. 11 and their spectrum (FIG. 12B), along with consecutive frames down-converted in real-time (FIG. 12C), and their edges coinciding with each other for I and Q channels (FIG. 12D).
Figure 12B:
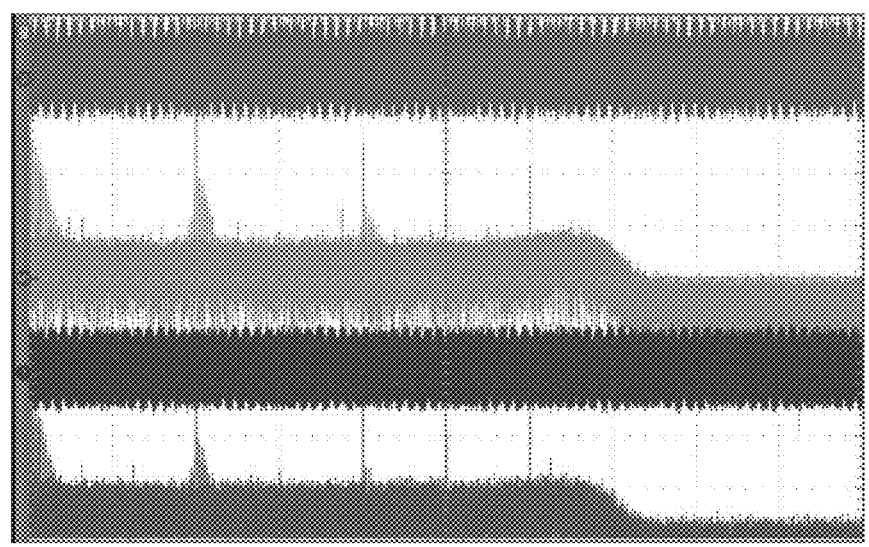
Figure 12C:
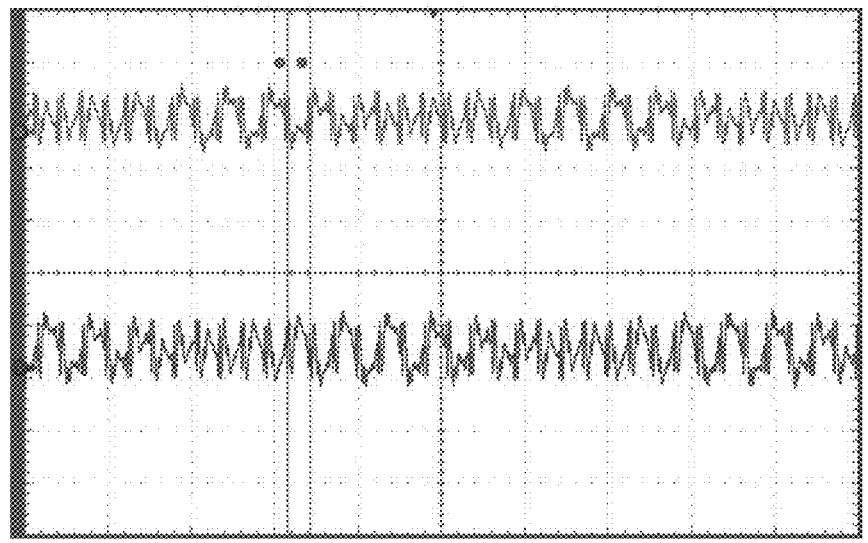
Figure 12D:
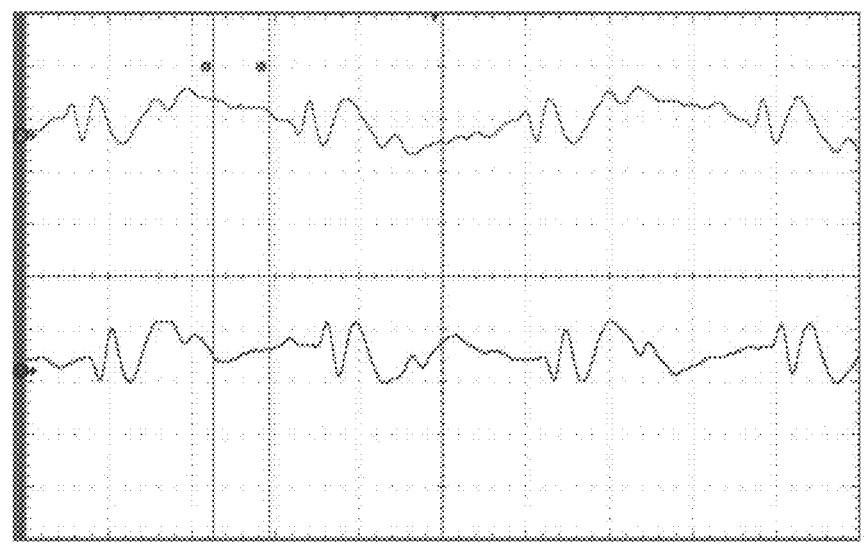

Referring now to the images of FIG. 12A through 12D, the I(t) and Q(t) signals are slowed-down in time (FIG. 12A) and down-converted in frequency domain (FIG. 12B) compared to the original Coherent-STEAM output 102. As shown in the image of FIG. 12C, this down-conversion is happening for consecutive frames at real-time. Also, both channels 120/122 may be configured to have the same group delay, and edges of the pulses in two channels can align as illustrated in the image of FIG. 12D).

Figure 13:
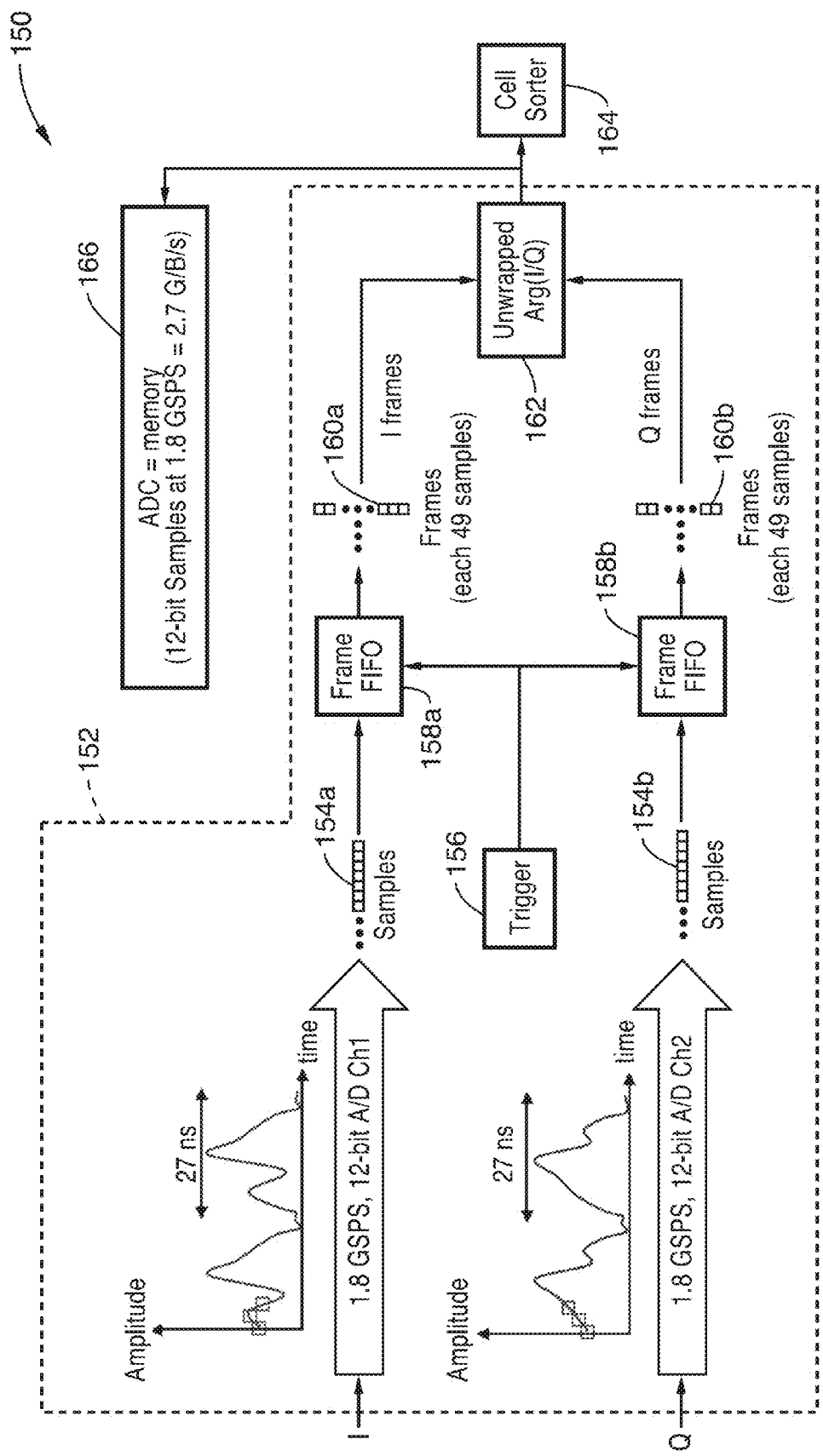
FIG. 13 is a schematic diagram of an exemplary digital signal processing FPGA for acquisition of analog signal processing system outputs.

The digital signal processing for derivation of sample phase-shift from the outputs I(t) and Q(t) of the analog signal processing system 100, can be easily implemented on an FPGA 150, as illustrated in FIG. 13.

In such exemplary embodiment, FPGA 150 may comprise a board 152 comprising argument calculator/trigger 156, unwrapper 162, and first in, first outs (FIFOs) 158a/158b for real-time processing of samples 154a/154b into I frames 160a and Q frames 160b. This is a direct result of transferring the cumbersome and calculation intensive parts of the sample phase recovery (Hilbert transformation) to an analog signal processing system. Also, this signal can be directly used to control a cell sorter 164 in a label-free imaging flow-cytometer and ADC 166.

It is appreciated that while the systems and methods disclosed above are illustrated for exemplary use in cell screening, however, it is appreciated that the systems and methods of the present disclosure may be applied to imaging a target that is either biological or non-biological specimen, i.e. the target may be non-living particles and is not limited to cells. The target motion is not limited to flow, and the target may be fixed and/or the imaging apparatus may be in motion.

Additional features may also include management and processing of digital data produced by STEAM implemented on a distributed processing cluster. Such distributed processing may include one or more of mapping, sorting, and reduction, wherein mapping is distributing the data within a cluster, sorting is organizing the data within the cluster based on the content, and reducing is summarizing the desired information into metadata Furthermore, said mapping may comprise distributing waveforms generated by STEAM, wherein the waveforms are acquired STEAM signals. In addition, sorting may comprise organizing the waveforms based on the signature of the samples contained in the waveforms, and reduction may comprise extracting and merging sample information from the waveforms.

In one exemplary embodiment, the management and processing of the digital data produced by STEAM are implemented by Apache Hadoop.

In summary, the novel system of the present description provides a type of imaging flow cytometry based on coherent stretched-time-encoded amplified microscopy, which is capable of classifying cells in flow rates as a high as a few meters per second. The novel coherent-STEAM method of the present disclosure measures size and total optical path difference of cells simultaneously, and extracts the refractive index, which corresponds to the protein concentration of the cells, as an additional parameter for classification. As illustrated in our experimental results, separation of two cell types was significantly enhanced by adopting the additional protein concentration parameter generated by Coherent-STEAM. Real-time analog signal processing of cell images and cell identification may be implemented on field-programmable gate arrays (FPGAs) for classification of many cell types.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. A system for phase contrast imaging of cells or dielectric particles in flow, comprising: an interferometer configured to map a phase image of the cells or dielectric particles into a spectrum of broadband optical pulses; a serial time-encoded amplified microscopy (STEAM) module; and a photodetector coupled to the interferometer and STEAM module; wherein the interferometer and STEAM module generate a coherent-STEAM output configured to simultaneously measure a size and optical phase shift of the cells or dielectric particles.

2. A system as in any of the previous embodiments, wherein the coherent-STEAM output is configured to simultaneously measure a size and optical density of the cells or dielectric particles.

3. A system as in any of the previous embodiments, wherein the coherent-STEAM output is configured to simultaneously measure a size and protein concentration of the cells.

4. A system as in any of the previous embodiments, wherein the coherent-STEAM output is configured for high-speed phase microscopy for label-free single-cell classification.

5. A system as in any of the previous embodiments, wherein the STEAM module is configured to chirp, stretch and amplify each optical pulse so that different wavelength components reach the photodetector serially.

6. A system as in any of the previous embodiments, wherein the STEAM module comprises a Raman amplifier and a dispersive fiber to perform dispersive Fourier transform.

7. A system as in any of the previous embodiments, further comprising: one or more optical reflective optical components coupled to the interferometer and STEAM module.

8. A system as in any of the previous embodiments, wherein the one or more optical components comprise reflection diffraction gratings and parabolic mirrors.

9. A system as in any of the previous embodiments, wherein the interferometer comprises a Michelson interferometer.

10. A system as in any of the previous embodiments, further comprising: a module for performing analog IQ demodulation of phase images of the coherent-STEAM output.

11. A system as in any of the previous embodiments, further comprising: a module for performing digital signal processing for interferometric STEAM.

12. A system as in any of the previous embodiments, the digital signal processing module configured for performing the steps of: digitizing and recording the coherent-STEAM output signal; saving each optical pulse in the output signal separately as a frame for further processing; generating an analytic form of each pulse and extracting a phase component of the analytic form; and combining phase line images generated from subsequent frames to form a spatial map of optical path difference.

13. A system as in any of the previous embodiments, further comprising: extracting a refractive index contrast between a cell and surrounding liquid as a function of the spatial map of optical path difference.

14. A system as in any of the previous embodiments, further comprising: a module for performing analog signal processing as a function of down-conversion of high-frequency spectral components of the Coherent-STEAM output.

15. A system as in any of the previous embodiments, wherein said analog signal processing module is configured to apply quadrature phase demodulation to retrieve cell measurements in real-time.

16. A system as in any of the previous embodiments, the analog signal processing module configured for performing the steps of: splitting the coherent-STEAM output signal into two signals; mixing the two split signals with two phase-shifted sinusoidal signals; and filtering a baseband component from the mixed signals.

17. A system as in any of the previous embodiments, wherein said analog signal processing module comprises an FPGA comprising: an argument calculator; first in, first out (FIFO); and an unwrapper.

18. A method for phase contrast imaging of cells or dielectric particles in flow, comprising: using an interferometer, mapping a phase image of the cells or dielectric particles into a spectrum of broadband optical pulses; chirping, stretching and amplifying each optical pulse so that different wavelength components are serially registered on a photodetector as a coherent serial time-encoded amplified microscopy (Coherent- STEAM) output; and simultaneously measuring a size and optical phase shift of the cells or dielectric particles.

19. A method as in any of the previous embodiments, further comprising simultaneously measuring a size and optical density of the cells or dielectric particles.

20. A method as in any of the previous embodiments, further comprising simultaneously measuring a size and protein concentration of the cells.

21. A method as in any of the previous embodiments, wherein the coherent-STEAM output is configured for high-speed phase microscopy for label-free single-cell classification.

22. A method as in any of the previous embodiments, wherein the STEAM module comprises a Raman amplifier and a dispersive fiber to perform dispersive Fourier transform.

23. A method as in any of the previous embodiments, further comprising: performing analog IQ demodulation of phase images of the coherent-STEAM output.

24. A method as in any of the previous embodiments, further comprising: performing digital signal processing for interferometric STEAM.

25. A method as in any of the previous embodiments, further comprising: digitizing and recording the coherent-STEAM output signal; saving each optical pulse in the output signal separately as a frame for further processing; generating an analytic form of each pulse and extracting a phase component of the analytic form; and combining phase line images generated from subsequent frames to form a spatial map of optical path difference.

26. A method as in any of the previous embodiments, further comprising: extracting a refractive index contrast between a cell and surrounding liquid as a function of the spatial map of optical path difference.

27. A method as in any of the previous embodiments, further comprising: performing analog signal processing as a function of down-conversion of high-frequency spectral components of the Coherent-STEAM output.

28. A method as in any of the previous embodiments, wherein performing analog signal processing comprises applying quadrature phase demodulation to retrieve cell measurements in real-time.

29. A method as in any of the previous embodiments, further comprising: splitting the coherent-STEAM output signal into two signals; mixing the two split signals with two phase-shifted sinusoidal signals; and filtering a baseband component from the mixed signals.

30. A method as in any of the previous embodiments, wherein the motion is not limited to flow.

31. A method as in any of the previous embodiments, wherein the target can be fixed or the imaging apparatus is in motion.

32. A method for management and processing of digital data produced by STEAM implemented on a distributed processing cluster.

33. A method as in any of the previous embodiments, wherein the distributed processing includes mapping, sorting, and reduction, wherein mapping is distributing the data within a cluster, sorting is organizing the data within the cluster based on the content, and reducing is summarizing the desired information into metadata.

34. A method as in any of the previous embodiments, wherein the said mapping is distributing waveforms generated by STEAM, wherein the waveforms are acquired STEAM signals, sorting is organizing the waveforms based on the signature of the samples contained in the waveforms, and reduction is extracting and merging sample information from the waveforms.

35. A method as in any of the previous embodiments, wherein the management and processing of the digital data produced by STEAM are implemented by Apache Hadoop.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A system for phase contrast imaging of cells or dielectric particles in flow, comprising:
    an interferometer configured to map a phase image of the cells or dielectric particles into a spectrum of broadband optical pulses;
    a serial time-encoded amplified microscopy (STEAM) module; and
    a photodetector coupled to the interferometer and STEAM module;
    wherein the interferometer and STEAM module generate a coherent-STEAM output configured to simultaneously measure a size and optical phase shift of the cells or dielectric particles.

2. A system as recited in claim 1, wherein the coherent-STEAM output is configured to simultaneously measure a size and optical density of the cells or dielectric particles.

3. A system as recited in claim 1, wherein the coherent-STEAM output is configured to simultaneously measure a size and protein concentration of the cells.

4. A system as recited in claim 3, wherein the coherent-STEAM output is configured for high-speed phase microscopy for label-free single-cell classification.

5. A system as recited in claim 1, wherein the STEAM module is configured to chirp, stretch and amplify each optical pulse so that different wavelength components reach the photodetector serially.

6. A system as recited in claim 5, wherein the STEAM module comprises a Raman amplifier and a dispersive fiber to perform dispersive Fourier transform.

7. A system as recited in claim 1, further comprising:
    one or more optical reflective optical components coupled to the interferometer and STEAM module.

8. A system as recited in claim 7, wherein the one or more optical components comprise reflection diffraction gratings and parabolic mirrors.

9. A system as recited in claim 1, wherein the interferometer comprises a Michelson interferometer.

10. A system as recited in claim 1, further comprising:
    a module for performing analog IQ demodulation of phase images of the coherent-STEAM output.

11. A system as recited in claim 1, further comprising:
    a module for performing digital signal processing for interferometric STEAM.

12. A system as recited in claim 11, the digital signal processing module configured for performing the steps of:
    digitizing and recording the coherent-STEAM output signal;
    saving each optical pulse in the output signal separately as a frame for further processing;
    generating an analytic form of each pulse and extracting a phase component of the analytic form; and
    combining phase line images generated from subsequent frames to form a spatial map of optical path difference.

13. A system as recited in claim 12, further comprising:
    extracting a refractive index contrast between a cell and surrounding liquid as a function of the spatial map of optical path difference.

14. A system as recited in claim 1, further comprising:
    a module for performing analog signal processing as a function of down-conversion of high-frequency spectral components of the Coherent-STEAM output.

15. A system as recited in claim 14, wherein said analog signal processing module is configured to apply quadrature phase demodulation to retrieve cell measurements in real-time.

16. A system as recited in claim 15, the analog signal processing module configured for performing the steps of:
    splitting the coherent-STEAM output signal into two signals;
    mixing the two split signals with two phase-shifted sinusoidal signals; and
    filtering a baseband component from the mixed signals.

17. A system as recited in claim 14, wherein said analog signal processing module comprises an FPGA comprising:
    an argument calculator;
    first in, first out (FIFO); and
    an unwrapper.

18. A method for phase contrast imaging of cells or dielectric particles in flow, comprising:
    using an interferometer, mapping a phase image of the cells or dielectric particles into a spectrum of broadband optical pulses;
    chirping, stretching and amplifying each optical pulse so that different wavelength components are serially registered on a photodetector as a coherent serial time-encoded amplified microscopy (Coherent- STEAM) output; and
    simultaneously measuring a size and optical phase shift of the cells or dielectric particles.

19. A method as recited in claim 18, further comprising simultaneously measuring a size and optical density of the cells or dielectric particles.

20. A method as recited in claim 18, further comprising simultaneously measuring a size and protein concentration of the cells.

21. A method as recited in claim 20, wherein the coherent-STEAM output is configured for high-speed phase microscopy for label-free single-cell classification.

22. A method as recited in claim 18, wherein the STEAM module comprises a Raman amplifier and a dispersive fiber to perform dispersive Fourier transform.

23. A method as recited in claim 18, further comprising:
    performing analog IQ demodulation of phase images of the coherent-STEAM output.

24. A method as recited in claim 18, further comprising:
    performing digital signal processing for interferometric STEAM.

25. A method as recited in claim 24, further comprising:
    digitizing and recording the coherent-STEAM output signal;
    saving each optical pulse in the output signal separately as a frame for further processing;
    generating an analytic form of each pulse and extracting a phase component of the analytic form; and combining phase line images generated from subsequent frames to form a spatial map of optical path difference.

26. A method as recited in claim 25, further comprising:
extracting a refractive index contrast between a cell and surrounding liquid as a function of the spatial map of optical path difference.

27. A method as recited in claim 18, further comprising:
performing analog signal processing as a function of down-conversion of high-frequency spectral components of the Coherent-STEAM output.

28. A method as recited in claim 27, wherein performing analog signal processing comprises applying quadrature phase demodulation to retrieve cell measurements in real-time.

29. A method as recited in claim 28, further comprising:
splitting the coherent-STEAM output signal into two signals;
mixing the two split signals with two phase-shifted sinusoidal signals; and
filtering a baseband component from the mixed signals.

* * * * *